United States Patent [19]

Flynn et al.

[11] Patent Number: 4,536,399
[45] Date of Patent: Aug. 20, 1985

[54] USE OF FUMED SILICA FOR TREATING OILY SKIN AND ACNE

[75] Inventors: Robert G. Flynn; Courtney G. Pitkin, both of St. Louis; Gregory A. Hileman, Hazelwood, all of Mo.

[73] Assignee: Norcliff Thayer, Inc., Tarrytown, N.Y.

[21] Appl. No.: 578,725

[22] Filed: Feb. 9, 1984

Related U.S. Application Data

[63] Continuation-in-part of Ser. No. 434,039, Oct. 13, 1982.

[51] Int. Cl.³ .................. A61K 31/60; A61K 31/075; A61K 31/695
[52] U.S. Cl. .................. 514/63; 424/DIG. 4; 424/69; 514/859; 514/938
[58] Field of Search .................. 424/184, 365, 69, 230, 424/338, DIG. 4

[56] References Cited

U.S. PATENT DOCUMENTS

| | | | |
|---|---|---|---|
| 2,435,005 | 1/1948 | Huppke et al. | 424/308 |
| 4,000,317 | 12/1976 | Menda et al. | 424/127 |
| 4,119,712 | 10/1978 | Goldner et al. | 424/69 |
| 4,189,501 | 2/1980 | Fulton, Jr. | 424/338 |

FOREIGN PATENT DOCUMENTS

| | | | |
|---|---|---|---|
| 2006345 | 8/1970 | Fed. Rep. of Germany | 424/365 |
| 2494714 | 5/1982 | France | 424/365 |
| 825452 | 12/1959 | United Kingdom | 424/69 |

OTHER PUBLICATIONS

Aerosil—Properties Relating to Use in Cosmetics, Ferch, 10/3/1969, pp. 1 to 24.

Primary Examiner—Dale R. Ore

[57] ABSTRACT

Therapeutic compositions containing fumed silica for the treatment of oily skin, and, optionally, containing benzoyl peroxide or salicylic acid for treatment of acne are disclosed.

6 Claims, No Drawings

USE OF FUMED SILICA FOR TREATING OILY SKIN AND ACNE

This is a continuation-in-part of application Ser. No. 434,039, filed Oct. 13, 1982.

BACKGROUND OF THE INVENTION

1. Field of the Invention

The invention relates to novel therapeutic compositions for the treatment of oily skin and acne.

The disease of *acne vulgaris* is reported to be the single most common skin disease and affects approximately eighty percent of the teenage population. However, it may persist into the third and fourth decades of life. Acne primarily is a disease of the pilosebaceous system with a multifactorial cause. The pathogenesis includes an androgen dependent increase in sebum production, proliferation of the *follicular microflora* (principally *P. acnes*) and alteration in the follicular keratinization. This results in the primary clinical lesions of acne, namely the open comedone (blackheads), closed comedone (whiteheads), papules, pustules, and nodules. The increased sebum production is responsible for the oily appearance. Currently therapy is directed towards treatment of the lesions. The presence of oil itself is not the cause of acne but is a great psychological problem for the acne patient.

The onset of *acne vulgaris* is related to adolescence and normal sexual and physical growth. During this rapid linear growth period there is a marked development in the pilosebaceous system which results in sebum production and changes in its composition and physical characteristics. These events are hormonally controlled.

The disease of the pilosebaceous follicle is first detectable by change occurring in the follicular epithelium. The pilosebaceous unit is made up of a hair follicle and a pilosebaceous gland which are connected to the skin surface by ducts through which the hair passes. The sebaceous gland produces sebum which is a mixture of fats and waxes that transgress the duct and spread to the skin surface which helps keep the skin soft and moist. The acne lesion develops when the gland and lining begin to work excessively which predominantly occurs during puberty. The glands produce more sebum making the skin oily. The duct normally sheds cells which are carried to the skin surface by the sebum. When acne develops, cells stick together to form a thick layer and plug the duct. More cells and sebum pile up behind this plug which results in the primary lesion of acne, the comedone. If the plug stays below the skin surface, it is called a "closed comedone" or a "whitehead." A comedone which pushes through the surface is referred to as an "open comedone" or "blackhead." This is not due to dirt but due to discloration or melanin, the dark pigment in normal skin. The whiteheads and blackheads are referred to as "noninflammatory acne lesions." However, the pilosebaceous unit can rupture and become inflamed and these are the pimples, papules, and pustules which are the inflammatory lesions of this disease.

Pilosebaceous units are found all over the body, but they are more predominant on the face, chest, and the back. These are usually the predominant areas which develop acne.

Prior Art

Current acne treatment is directed toward reduction of the lesions and it is usually quite effective. Topical/oral antibiotics, benzoyl peroxide, sulfur, retinoic acid, and salicylic acid, are quite effective in controlling the lesions. However, the sebum and oily appearance of the acne patient's face is still a problem and therefore many of these materials are combined with oil absorbing ingredients such as bentonite which has long been used to control the vexing problem of skin oil. Other compositions of the prior art contain pyrogenic fumed silica in oil-free suspensions for application to oily skin. While many of these compositions can be used to advantage, it would be desirable to have improved compositions for the treatment of oily skin and acne.

SUMMARY OF THE INVENTION

The present invention provides therapeutically effective compositions containing fumed silica for treating oily skin. Optionally, the compositions contain an antibacterial compound, such as benzoyl peroxide and/or a karatolytic agent, such as salicylic acid for acne treatment.

The composition of the present invention comprises: fumed silica from about 1–10% w/w in a topical vehicle that is cosmetically acceptable for frequent application to the skin without showing the presence of deposit or film thereon and which performs as a lotion or creme conventionally used as part of the beauty regimen.

The vehicle or carrier for the fumed silica can be characterized as an oil-in-water emulsion. The oil portion of the emulsion comprises a high molecular weight fatty alcohol the preferred member of which is cetyl alcohol. It has been found that cetyl alcohol, when present in the range of about 1 to 4% w/w and preferably 1.5 to 3% w/w in the formulations of the present invention, provides the most beneficial effects. Cetyl alcohol is a thickening agent/emollient and provides the desired viscosity, appearance and feel to the formulations. In addition to high molecular weight fatty alcohols other oily compounds can be used with or in place of high molecular weight fatty alcohols, such as fatty acids, the preferred member of which is stearic acid, and glycol esters, the preferred member of which is glycerol monostearate.

An emulsifier is used to emulsify the oil-in-water. We prefer to use the anionic surface active agent, sodium lauryl sulfate, as the emulsifyier in the range of about 0.25 to 1.5% w/w and preferably 0.5% to 1.0% w/w.

In addition to the essential ingredients other cosmetic excipients may be used to advantage in the formulations. Such excipients include 0.25%–2% w/w propylene glycol as a humectant or skin softener, 0.1–2% w/w citric acid/sodium citrate buffer to adjust the ionic strength of the formulations to the normal pH of the skin, and methyl paraben/propyl paraben as a preservative system to protect the formulations from bacterial growth.

DETAILED DESCRIPTION OF THE INVENTION

The inventors have found that fumed silica is particularly effective in reducing the oily appearance of skin.

Fumed silica is a synthetic, amorphous, colloidal silicon dioxide. It is produced by the vapor hydrolysis of chlorosilanes, such as silicon tetrachloride, in a hydrogen-oxygen flame:

$$SiCl_4 + 2H_2 + O_2 \xrightarrow{1800°\ C.} SiO_2 + 4HCl$$

In the combustion process, molten spheres of amorphous silica are formed. These particles are produced in various sizes, ranging from 7 to 21 nanometers in diameter yielding a surface area of 400 to 130 square per gram. These primary particles collide and fuse, to form branched, three-dimensional, chain-like aggregates. Further agglomeration takes place below the fusion temperature, until the size of the agglomerates ranges from approximately 0.5 to 10 microns.

Fumed silica meets all of the requirements for "Colloidal Silica Dioxide" as described in the USP—National Formulary.

A preferred fumed silica is CAB-O-SIL sold by the Cabot Corporation.

CAB-O-SIL fumed silica is pure commercially available amorphous silica. It is at least 99.8 percent by weight silicon dioxide on an ignited weight basis. Typical levels of trace metallic impurities are shown below:

| Typical Analysis of CAB-O-SIL for Trace Metallic Contaminants ||||||
| --- | --- | --- | --- | --- | --- |
| Element | ppm | Element | ppm | Element | ppm |
| Ag | 0.1 | Cr | 1 | P | 3 |
| Al | 2 | Cu | 0.5 | Pb | 0.1 |
| As | 0.2 | Fe | 2 | Sb | 0.1 |
| B | 2 | Hg | 0.1 | Se | 0.1 |
| Ba | 1 | Li | 0.1 | Sn | 1 |
| Be | 0.5 | Mg | 0.5 | Ti | 2 |
| Bi | 2 | Mn | 0.5 | V | 2 |
| Ca | 2 | Mo | 2 | Zn | 1 |
| Cd | 0.1 | Na | 5 | Zr | 5 |
| Co | 0.5 | Ni | 2 | | |

The amounts listed above mean that the element was not detected at the level given. These data do not represent a guarantee or specification but simply show typical values found when random production samples were treated by various analytical methods.

Many agents were investigated to determine their oil absorption potential. These agents included kaolin, aluminum hydroxide, precipitated silica, and fumed silica. Fumed silica was found to be substantially superior to the other agents. The property of the ability to absorb skin oil is determined by using the ASTM method for oil absorption. Squalene, the principal oil found in sebum, is used as the oil to be absorbed. See Table 1 below for the results of the investigation.

TABLE 1

| OIL ABSORPTION CAPACITY OF VARIOUS INGREDIENTS AS DETERMINED BY ASTM RUBOUT METHOD* ||
| --- | --- |
| Bentonite | 50.1 g |
| Aluminum Hydroxide | 52.7 g |
| Georgia Kaolin Bentonite | 57.0 g |
| Microfine Bentonite | 51.0 g |
| Syloid 244 Silica Precipitated | 275 g |
| Silica Fumed | 428 g |

*Results expressed as grams of oil absorbed per 100 grams of sample.

An in vivo test was undertaken to assess the oil absorption properties of a formulation containing fumed silica in relationship to the generally recognized effective oil absorbing agent, bentonite, which is commercially available in several over-the-counter preparations.

The experimental design utilizes an indirect method of analysis based on partitioning of the oil between an absorbent pad and the agent. Since squalene is the major component in skin oil and it is shown to be easily and readily extracted from polyester absorbent pads, but not from certain composition preparations, it was determined that the oil which was on the skin was being absorbed preferentially by the product and would not migrate to the pad.

To test the oil absorption property of the product, it was applied to a specific place on the forehead and the area was covered with a polyester pad. The second pad of identical surface area was applied to an untreated portion of the forehead to serve as a blank. Skin lipids squalene, cholesterol and oleic acid were analytically determined by extraction with chloroform and assayed by gas chromatography. The total available lipids were determined from the blank pad. The amount absorbed was determined by substracting micrograms of lipids on the product pad from the micrograms of lipids on the blank pad. The samples were collected over a six hour period—at three, four and six hours. The results were as follows:

| AMOUNTS OF MCG OF SQUALENE ABSORBED ||||
| --- | --- | --- | --- |
| | Commercial Product A | Commercial Product A with Fumed Silica | Commercial Product B with Bentonite |
| 3 Hours | 30 | 40 | 40 |
| 4 Hours | 65 | 135 | 110 |
| 6 Hours | 75 | 150 | 100 |

The agent, fumed silica, is incorporated in an oil-in-water emulsion which, as demonstrated in the examples below, can be combined with therapeutically active agents such as benzoyl peroxide, a recognized antibacterial and salicyclic acid, which is a recognized karatolytic. In addition, the agent and lotion containing only the fumed silica compound is provided to treat seborrhea or excessive oiliness or it can absorb the excessive liquids in other disease states such as poison ivy, diaper rash.

The composition contains from 1–10% by weight of fumed silica, preferably 1.5–3%.

When the composition also contains other agents such as benzoyl peroxide or salicylic acid, such agents may be present up to about 10% w/w.

The following examples show the use of fumed silica which, when combined with other therapeutically active agents, provide formulations that are useful not only in the treatment of acne lesions, but also provide a cosmetic benefit due to the oil absorption characteristics of the product.

EXAMPLE 1

Oil Absorbing/Antibacterial Formula

| | Percent (Approximate) |
| --- | --- |
| Cetyl Alcohol | 2.1 |
| Propylene Glycol | 1.0 |
| Buffer | 1.0 |
| Preservative | 0.25 |
| Sodium Lauryl Sulfate | 0.5 |
| Fumed Silica (Amorphous) | 2.0 |
| Benzoyl Peroxide | 10.0 |
| Purified Water Up To: | 100% |

The composition is made as follows:

(1) Melt together cetyl alcohol and preservatives and heat 10° C. above melting point.

(2) Combine all other ingredients except benzoyl peroxide and heat to 10° C. above melting point of wax phase.

(3) Rapidly mix an equal volume of aqueous phase with wax phase for five minutes to make a primary emulsion.

(4) Rapidly mix a 3-fold volume of aqueous phase with the primary emulsion and mix five minutes while maintaining hot temperature.

(5) Pour second emulsion into remaining aqueous phase and mix slowly while cooling.

(6) When cooled, add benzoyl peroxide, mix well and mill to appropriate particle size.

EXAMPLE 2

Oil Absorbing/Antibacterial Formula

|  | Percent (Approximate) |
|---|---|
| Cetyl Alcohol | 2.1 |
| Glyceryl Stearate and PEG 100 Stearate | 2.0 |
| Steareth 20 | 2.0 |
| Buffer | 1.0 |
| Preservative | 0.20 |
| Fumed Silica | 2.0 |
| Benzoyl Peroxide | 10.0 |
| Purified Water Up To: | 100% |

The composition is made as follows:

(1) Melt together cetyl alcohol, glyceryl stearate and PEG 100 Stearate, Steareth-20 and preservatives. Heat 10° C. above melting point.

(2) Combine all other ingredients except benzoyl peroxide and heat to 10° C. above melting point of wax phase.

(3) Rapidly mix an equal volume of aqueous phase with wax phase for five minutes to make a primary emulsion.

(4) Rapidly mix a 3-fold volume of aqueous phase with the primary emulsion and mix five minutes while maintaining hot temperature.

(5) Pour second emulsion into remaining aqueous phase and mix slowly while cooling.

(6) When cooled, add benzoyl peroxide, mix well and mill to appropriate particle size.

EXAMPLE 3

Oil Absorbing Emollient Lotion

|  | Percent (Approximate) |
|---|---|
| Glyceryl Monostearate | 2.0 |
| Cetyl Alcohol | 2.5 |
| Stearic Acid | 2.0 |
| Preservative | 0.25 |
| Buffer | 1.0 |
| Sodium Lauryl Sulfate | 1.0 |
| Propylene Glycol | 2.0 |
| Fumed Silica | 2.0 |
| Benzoyl Peroxide | 10.0 |
| Water Up To: | 100% |

The composition is made as follows:

(1) Melt glyceryl monostearate, cetyl alcohol, stearic acid and preservative. Mix and heat to 10° C. above melting point.

(2) Add remaining ingredients except benzoyl peroxide to water and mix while heating to 10° C. above melting point of waxes.

(3) Slowly add wax phase and mix slowly until uniform. Cool to room temperature.

(4) Add benzoyl peroxide, mix well, and mill to appropriate particle size.

EXAMPLE 4

Oil Absorbing Emollient Lotion

|  | Percent (Approximate) |
|---|---|
| Cetyl Alcohol | 2.0 |
| Propylene Glycol | 1.0 |
| Buffer | 1.0 |
| Preservative | 0.20 |
| Sodium Lauryl Sulfate | 0.5 |
| Fumed Silica | 2.0 |
| Purified Water Up To: | 100% |

The composition is made as follows:

(1) Melt cetyl alcohol and preservative together. Heat to 10° C. above melting point of waxes.

(2) Combine all other ingredients and heat to 10° C. above melting point of wax phase.

(3) Rapidly mix an equal volume of aqueous phase with wax phase for five minutes to make a primary emulsion.

(4) Rapidly mix a 3-fold volume of aqueous phase with the primary emulsion and mix five minutes while maintaining hot temperature.

(5) Pour second emulsion into remaining aqueous phase and mix slowly while cooling.

(6) When cooled, mix well and mill to appropriate particle size.

EXAMPLE 5

Oil Absorbing/Keratolytic Formula

|  | Percent (Approximate) |
|---|---|
| Ceteth-10 | 17.0 |
| Oleth-20 | 5.0 |
| Methyl Gluceth-20 Sequisterate | 5.0 |
| Mineral Oil/Lanolin Alcohol | 8.0 |
| Methyl Gluceth 10 | 5.0 |
| Silica Fumed | 1.8 |
| Salicylic Acid | 3.0 |
| Water Q.S. | 100% |

The composition is made as follows:

(1) Melt and mix together Ceteth-10, Oleth 20, Methyl Gluceth-20, Sequistearate and Salicylic Acid. Mix until clear hot solution forms.

(2) Add Methyl Gluceth-10 to water and heat to same temperature as wax phase. Mix until dissolved. Disperse silica and mix well.

(3) Slowly pour hot oil mixture into water phase with very little mixing. Allow to cool with little or no mixing.

In vivo comparative experiments were carried out as shown below using the composition of Example A according to the present invention, and two "non-oily" compositions, Examples B and C, of the prior art.

COMPOSITION OF FORMULAE TESTED

Example A

| Ingredients | % w/w |
|---|---|
| Cetyl Alcohol | 2.1 |
| Amorphous Fumed Silica | 1.8 |
| Benzoyl Peroxide | 10.0 |
| Propylene Glycol | 1.0 |
| Sodium Lauryl Sulfate | 0.5 |
| Preservatives (Methyl- and Propyl-Paraben) | 0.25 |
| Citric Acid & Sodium Citrate - Buffer | 1.0 |
| Purified Water Up To: | 100.0 |

The composition of Example A was made as described for Example 1.

Example B

| Ingredients | % W/W | Amount/g. |
|---|---|---|
| Cab-O-Sil M5 | 2.5 | 12.5 |
| NaCMC(7HOF) | 0.5 | 2.5 |
| Glycerol | 1.0 | 5.0 |
| Water | 81.0 | 405.0 |
| Ethanol SD-40 | 15.0 | 75.0 |
| | 100.0% | 500.0 g. |

Procedure used to make the formula of Example A:
(1) NaCMC was dispersed in ethanol using a Boorfield counter-rotating mixer;
(2) Glycerol was added followed by thorough mixing;
(3) Cab-O-Sil was dispersed in water and then added to the alcohol phase with mixing;
(4) Mixing was continued for 15 minutes; and
(5) Homogenized by hand.

Example C

| Ingredients | % W/W | Amount/g. |
|---|---|---|
| Cab-O-Sil M5 | 2.0 | 10.0 |
| Veegum | 0.5 | 2.5 |
| Klucel MF | 1.0 | 5.0 |
| NA$_2$ EDTA | 0.025 | 0.125 |
| Water | 48.975 | 244.875 |
| Alcohol | 47.5 | 237.500 |
| | 100.0% | 500 g. |

Procedure used for making the composition of Example C:
(1) Klucel was slowly added to alcohol with stirring, mixing was continued for 1 hour;
(2) Cab-O-Sil was dispersed in about 73 g. of water and mixing was continued until uniform dispersion was obtained;
(3) With stirring, the Cab-O-Sil dispersion (2) was added to the Klucel dispersion (1);
(4) To the remaining water (171,875 g) at 80° C., Na$_2$EDTA and Veegum were added with rapid stirring, followed by mixing for 15 minutes at 80° C. to hydrate Veegum and then the mixture was cooled to room temperature; and
(5) The mixture obtained in step 3 was slowly added with mixing to the mixture obtained in step 4 until satisfactory dispersion obtained.

Clinical Procedure For Testing the Above-Identified Formulae

1. Six subjects, four male and two female, were used in the testing;
2. For each subject, the forehead area was swabed with ethanol-moistened tissue to remove residual sebum;
3. The forehead was allowed to dry;
4. Using a randomly generated application code, 0.1 ml. of the product was applied to one side of the forehead and massaged into the skin until the product has almost completely vanished;
5. To each side of the forehead a piece of absorbent pad measuring ½"×2" was affixed and covered with a double layer of fiberglass screen. The fiberglass screen was secured to the forehead with a 1"-wide micropore tape;
6. At 3, 6 and 8 hour intervals ½"×½" sections of the pad was removed;
7. Each pad removed was placed in a labeled vial for chromatographic analysis.

Analytical Procedure

1. Each "blank" and each "sample" was extracted with 0.2 ml of carbon tetrachloride;
2. 3 mcl of the extract was injected into the gas chromatograph with the following conditions:
3% OV-17 on 100/120 mesh gas chrom Q column N$_2$ carrier at a flow rate of 30 ml/min.
Column conditions:
225° C. for 2 min.
225°–330° C. at 5° C./min.
Hold 300° C. for 2 min.
FID attenuated as needed.

Calculation of Result

The "blank" pad indicates the amount of squalene (oil) present on the subject's skin surface. The "product" pad represents the amount of squalene not absorbed by the sample product. (Squalene is readily extracted from the pad but not from the product with the given analytical procedure).

The data for each individual was calculated, using the chromatographic chart, by subtracting the "sample" from the "blank", i.e., the amount of squalene available for absorption minus the amount not absorbed. The individual data was then averaged to give the "composite" data as shown hereunder.

Microgram Squalene Absorbed/sq.in

| Subject | Hour | Example A | Example B | Example C |
|---|---|---|---|---|
| Composite | 3 | 37.6 | 46.4 | 46.2 |
| " | 6 | 252.1 | 85.1 | 146.5 |
| " | 8 | 318.0 | 118.6 | 167.7 |

Additionally, formulas of the present invention which contained no benzoyl peroxide were tested for oil absorption. The results obtained were similar to the results of Example A.

What is claimed is:
1. A composition for application to oily skin consisting essentially of by weight:
1–10% fumed silica consisting of 99.8% silicone dioxide on an ignited weight basis and capable of absorbing about 4 gm of squalene oil per gm, in an oil-in-water emulsion carrier, said carrier consisting of 1-4% of a thickening agent/emollient selected from the group consisting of cetyl alcohol, stearic acid and glycerol monostearate, 0.25-1.5% sodium lauryl sulfate emulsifier and water q.s. 100%.

2. A method of treating oily skin in humans comprising topically applying an amount effective to treat oily skin of the composition of claim 1.

3. A composition for application to oily skin consisting essentially of by weight:

1-10% benzoyl peroxide;

1-10% fumed silica consisting of 99.8% silicone dioxide on an ignited weight basis and capable of absorbing about 4 gm of squalene oil per gm, in an oil-in-water emulsion carrier, said carrier consisting of 1-4% of a thickening agent/emollient selected from the group consisting of cetyl alcohol, stearic acid and glycerol monostearate, 0.25-1.5% sodium lauryl sulfate emulsifier, and water q.s. 100%.

4. A method of treating acne in humans comprising topically applying an amount effective to treat acne of the composition of claim 3.

5. A composition for application to oily skin consisting essentially of by weight:

1-10% salicylic acid;

1-10% fumed silica consisting of 99.8% silicone dioxide on an ignited weight basis and capable of absorbing about 4 gm of squalene oil per gm, in an oil-in-water emulsion carrier, said carrier consisting of 1-4% of a thickening agent/emollient selected from the group consisting of cetyl alcohol, stearic acid and glycerol monostearate, 0.25-1.5% sodium lauryl sulfate emulsifier, and water q.s. 100%.

6. A method of treating acne in humans comprising topically applying an amount effective to treat acne of the composition of claim 5.

* * * * *